United States Patent [19]

Viscomi et al.

[11] Patent Number: 5,043,423

[45] Date of Patent: Aug. 27, 1991

[54] METHOD FOR PURIFYING LOW MOLECULAR WEIGHT COMPOUNDS OF PEPTIDE OR PSEUDO-PEPTIDE STRUCTURE

[75] Inventors: Giuseppe C. Viscomi, Siena; Franco Cardinali; Maria G. Longobardi, both of Rome, all of Italy

[73] Assignee: Sclavo S.p.A., Siena, Italy

[21] Appl. No.: 573,687

[22] Filed: Aug. 28, 1990

[30] Foreign Application Priority Data

Sep. 4, 1989 [IT] Italy .................................. 21613 A/89

[51] Int. Cl.$^5$ ............................ C07K 1/14; C07K 5/08
[52] U.S. Cl. ..................................... 530/344; 530/331
[58] Field of Search ....................... 530/330, 331, 344; 210/672, 674

[56] References Cited

U.S. PATENT DOCUMENTS 3,778,426 12/1973 Najjar .................................. 530/331
4,855,405 8/1989 Yoshioka et al. ................... 530/330

FOREIGN PATENT DOCUMENTS 253190 1/1988 European Pat. Off. .

OTHER PUBLICATIONS

Horvath et al., "Operating Parameters in High-Performance Discplacement Chromatography," J. Chromatogr. 255, 273-93 (1983).

Primary Examiner—Jeffrey E. Russel
Attorney, Agent, or Firm—Birch, Stewart, Kolasch & Birch

[57] ABSTRACT

This invention firstly provides a method for purifying particular compounds of peptide or pseudo-peptide structure in which the number of protonable basic functions is greater than the number of acid functions and which have a molecular weight of less than 1000 daltons, by ion exchange displacement chromatography. In the method of the present invention the stationary phase used is a cationic exchange resin or a cross-linked polymer matrix activated with acid groups; the transporter solvent used is water if the compound to be purified already possesses at least one net positive charge, or aqueous dilute solutions of inorganic or strong organic acids which protonate the basic groups of the peptide or pseudo-peptide to be separated without modifying the structure of the peptide compound, such as acetic acid, trifluoroacetic acid, formic acid, hydrochloric acid or sulphuric acid; the displacer compound used is a triethylenetetraammonium salt.

10 Claims, No Drawings

METHOD FOR PURIFYING LOW MOLECULAR WEIGHT COMPOUNDS OF PEPTIDE OR PSEUDO-PEPTIDE STRUCTURE

This invention relates to a new method for purifying compounds of peptide or pseudo-peptide structure.

More particularly, the invention relates to a new method for purifying peptides or pseudo-peptides having a molecular weight of less than 1000 daltons and a number of protonable basic functions greater than the number of acid functions, so that the corresponding protonated form possesses one, two or three net positive charges.

In other words, the peptides or pseudo-peptides which can be purified by the method of the present invention are those low molecular weight peptides or pseudo-peptides in which the balance between the protonable basic groups present in the side chain or in the terminal positions of the main chain and the acid groups also present in the side chain or in the terminal positions of the main chain is positive, and in particular those compounds in which the number of protonable basic groups exceeds the number of acid groups by 1, 2 or 3.

The method of the present invention consists of subjecting the peptide or pseudo-peptide to be isolated or purified, to ion exchange displacement chromatography under suitable conditions.

The present invention also relates to the use of the new method for purifying tuftsin, synthetic tuftsin analogues such as those described by J. Martinez and F. Winternitz in Annals of the New York Academy of Sciences, volume 419, 1983, and tuftsin retro-inverso peptide analogues of the formula (I)

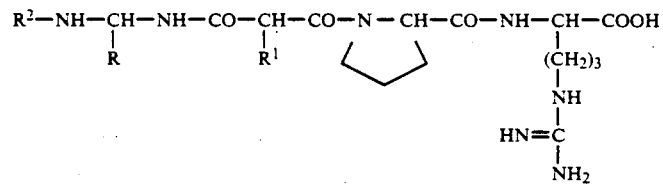

where
R can be a —CH(OH)CH$_3$, —CH$_2$—CH$_2$—S—CH$_3$ or —CH$_2$—CH(CH$_3$)$_2$ group,
R$^1$ represents a —(CH$_2$)$_4$—NH$_2$ or —(CH$_2$)$_3$—NH—C(=NH)NH$_2$ group, and
R$^2$ is hydrogen or a metabolically labile acyl group, such as the compounds described in EP-A-253,190.

Displacement chromatography is a chromatography method, described in 1943 by Tiselius, which uses commercially available chromatographic supports, eluents and apparatus conventionally used in linear elution chromatography, and is characterised by the presence of a compound known as a displacer which must have the property of being more strongly adsorbed on the stationary phase than each component of the mixture to be separated or purified.

In the displacement method, the stationary phase is firstly balanced with a solvent known as a transporter, which is chosen on the basis of its low affinity for the stationary phase and its capacity to dissolve the components of the mixture to be separated or purified, as in the case of the displacer compound, even at high concentration. The mixture to be purified is thus fed into the column in a quantity such as to completely saturate the initial part of the column. A solution of the displacer compound is then pumped into the column until the stationary phase is completely saturated. During this latter stage the mixture components move along the column under the force of the displacer solution. More precisely, the more strongly adsorbed mixture components displace from the surface of the stationary phase those which have a milder interaction, until by this competitive adsorption mechanism a separation of the components is obtained in the form of adjacent bands of uniform concentration, the sequence of which depends on their degree of affinity with the stationary phase.

The advantages of displacement chromatography over elution chromatography are in general terms the following: a greater quantity of purified product per unit of stationary phase; a high chromatographic yield; a reduced solvent consumption with consequent lower industrial costs; higher concentration of purified product in the eluate and thus easier product recovery from the effluent.

Displacement chromatography would therefore seem to be a method of extreme interest, mainly for separations on a preparative scale. In particular, the application of this method in the biological field has been recently studied in terms of certain special aspects [see H. Kalasz et al., J. Chromatography, 215 (1981) p. 295 onwards; J. H. Frenz et al., J. chromatography, 330 (1985) p. 1 onwards; G. Vigh et al., J. Chromatography, 394 (1987), p. 305 onwards; G. C. Viscomi et al., J. Chromatography, 440 (1988), p. 157 onwards], and the purification of certain peptide compounds by reverse phase displacement chromatography has been described in detail.

The present invention firstly provides a method for purifying particular compounds of peptide or pseudo-peptide structure having a molecular weight of less than 1000 daltons and one, two or three net positive charges when in the protonated form, by ion exchange displacement chromatography. In the method of the present invention the stationary phase used is a cationic exchange resin or a cross-linked polymer matrix activated with acid groups. The transporter solvent used is water or aqueous dilute solutions of inorganic or strong organic acids which protonate the basic groups of the peptide or pseudo-peptide to be separated without modifying the structure of the peptide compound, such as acetic acid, trifluoroacetic acid, formic acid, hydrochloric acid or sulphuric acid. The displacer compound used is a triethylenetetraammonium salt. In this respect, the use of triethylenetetraammonium salts, the use of which as a displacer in displacement chromatography has never been described, has proved extremely advantageous in the purification of certain low molecular weight peptides and pseudo-peptides.

In practice, the column used is a conventional chromatography column, preferably a column for high resolution chromatography, packed with a stationary phase consisting of an organic or inorganic polymer activated with preferably strongly acid groups such as carboxylic or sulphonic groups, preferably in the form of small particles having a mean diameter of between 2 and 80 μm, and more preferably between 5 and 50 μm.

Once the operating conditions in terms of flow and concentration of the various species have been fixed for a given separation, the optimum column length for sharp separation of the mixture components depends on the quantity of substance to be purified. In this respect, the column must be of sufficient length to accommodate the isotachic sequence of adjacent bands.

When the column has been prepared, the chosen transporter solvent is water, if the peptide or pseudo-peptide to be purified is already in charged form, or inorganic or strong organic acid solutions if the peptide or pseudo-peptide is in neutral or not completely charged form, and depending on the solubility of the starting mixture in it and its capacity to elute the mixture components from the stationary phase, which must, as stated, be the lowest possible.

If acid solutions are used, the acid concentration is generally between 0.5 and 10 mmoles/liter and preferably between 1 and 5 mmoles/liter. The transporter solvent is firstly used to balance the column and then to dissolve the initial mixture to be purified.

The solution obtained is then diluted with the transporter solvent until it reaches an ionic force such as to allow its complete adsorption on the cationic exchange resin.

The ratio of quantity of mixture to be purified fed into the column to the volume of the stationary phase is kept between 10 and 100 mg/ml to prevent overloading of the column, which could result in incomplete separation.

When the solution containing the mixture to be separated has been prepared, this is fed into the column after which the solution of the displacer compound is pumped through the column, this compound in the purification method of the present invention being a triethylenetetraamine acid addition salt.

The optimum concentration of the displacer compound in the transporter solvent is typically between 1 and 100 mmoles/liter and preferably between 25 and 75 mmoles/liter, the linear flow rate with which this solution is passed through the column being maintained between 0.005 and 0.04 cm/sec.

The effluent is collected in fractions of suitable volume, the content of which is analyzed by conventional analytical methods. When analysis shows that the fraction contains the displacer compound the chromatographic run is suspended and the column regenerated if required. Regeneration is easily achieved by washing with aqueous solutions of acid salts having an ionic strength of at least 200 times that of the displacer solution, and then with water.

The advantages of the method of the present invention over the conventional linear elution methods are the reduced chromatography time, which is approximately about ⅓-⅕ of the time required for elution chromatography; the greater quantity of product loaded per ml of stationary phase (about 10 times greater); and the higher concentration of the purified product (10-100 times higher) in low salt concentration eluents, with consequent reduced recovery time and cost. The compound to be purified is collected in the form of a salt of acid addition, the counter-ion of which is that of the triethylenetetraammonium salt used as the displacer. If desired, the compound can be converted into the corresponding free base by known methods.

The purpose of the following example is merely to illustrate the process of the present invention in certain of its representative aspects, and must not be interpreted as representing a limitation on the scope of the invention.

EXAMPLE

Purification of [gThr$^1$,m(R,S)Lys$^2$]Tuftsin

A 10 mm diameter glass column is packed with 34.5 ml of Sepharose S resin (45-165 μm, Pharmacia).

The column is conditioned with a 1 mM aqueous HCl solution. A solution of the compound obtained as the lyophilized product in step 1 of Example 1 in EP-A-253,190 (800 mg with a purity of 46%) in the 1 mM HCl solution (1000 ml) is then fed into the column at a flow rate of 2 ml/min.

When the feed is complete, a 50 mM triethylenetetraamine solution adjusted to pH 3 with concentrated HCl is pumped in. After 81 ml, the head of the displacer solution emerges from the column, at which time the chromatography run is suspended and the column washed with a 1M aqueous ammonium chloride solution (30 ml) and water (70 ml).

The pure product is collected from 70 to 77 ml of eluate, with a mean concentration in the pooled fractions of 38.5 mg/ml. The product obtained has a purity exceeding 95%. The chromatographic yield is 85%.

We claim:

1. A method for purifying compounds of peptide or pseudo-peptide structure having a molecular weight of less than 1000 daltons and a number of protonable basic functions present in the side chain or in the terminal positions of the main chain greater than the number of acid functions by one, two or three, consisting of subjecting a mixture containing the desired product to ion exchange displacement chromatography, using as stationary phase a cationic exchange resin, as transporter solvent water or an aqueous dilute solution of inorganic or strong organic acids in a concentration of between 0.5 and 10 mmoles/liter, which protonate the basic groups of the peptide or pseudo-peptide to be separated without modifying their structure, and as displacer compound a triethylenetetraammonium salt.

2. The method of claim 1 for purifying tuftsin, synthetic tuftsin analogues and tuftsin retro-inverso peptide analogues of the formula (I)

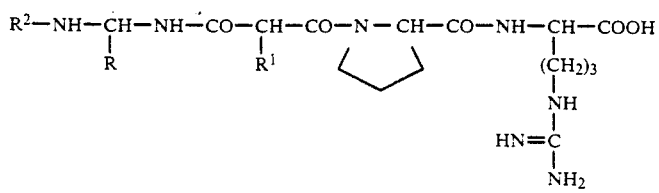

where
R is a —CH(OH)CH$_3$, —CH$_2$—CH$_2$—S—CH$_3$ or —CH$_2$—CH(CH$_3$)$_2$ group, $R^1$ represents a $-(CH_2)_4-NH_2$ or $-(CH_2)_3-NH-C(=NH)NH_2$ group, and $R^2$ is hydrogen or a metabolically labile acyl group.

3. The method of claim 2 for purifying tuftsin retro-inverso analogues of the formula (I).

4. The method of claim 1 wherein the inorganic or strong organic acid possibly contained in the transporter solvent is chosen from acetic acid, trifluoroacetic acid, formic acid, hydrochloric acid and sulphuric acid.

5. The method of claim 1 wherein the concentration of the inorganic or strong organic acid contained in the transporter solvent is between 1 and 5 mmoles/liter.

6. The method of claim 1 wherein the stationary phase consists of an organic or inorganic polymer activated with acid groups and in the form of small particles, having a mean diameter of between 2 and 80 μm.

7. The method of claim 6 wherein the particle diameter is between 5 and 50 μm.

8. The method of claim 6, wherein the acid groups are carboxyl or sulphonic groups.

9. The method of claim 1 wherein the displacer compound concentration in the transporter solvent is between 1 and 100 mmoles/liter.

10. The method of claim 9 wherein the displacer concentration is between 25 and 75 mmoles/liter.

* * * * *